(12) United States Patent
Pyles et al.

(10) Patent No.: US 8,170,674 B2
(45) Date of Patent: May 1, 2012

(54) METHOD OF USING SPINAL CORD STIMULATION TO TREAT GASTROINTESTINAL AND/OR EATING DISORDERS OR CONDITIONS

(75) Inventors: Stephen Pyles, Ocala, FL (US); Rohan Hoare, Dallas, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 334 days.

(21) Appl. No.: 12/039,165

(22) Filed: Feb. 28, 2008

(65) Prior Publication Data

US 2008/0154329 A1     Jun. 26, 2008

Related U.S. Application Data

(63) Continuation of application No. 11/234,960, filed on Sep. 26, 2005.

(60) Provisional application No. 60/613,495, filed on Sep. 27, 2004, provisional application No. 60/614,312, filed on Sep. 29, 2004.

(51) Int. Cl.
*A61N 1/00* (2006.01)

(52) U.S. Cl. .......................................... 607/40; 607/117

(58) Field of Classification Search .............. 607/40–41, 607/117
See application file for complete search history.

(56) References Cited

U.S. PATENT DOCUMENTS

| | | |
|---|---|---|
| 3,654,933 A | 4/1972 | Hagfors |
| 3,724,467 A | 4/1973 | Avery et al. |
| 3,822,708 A | 7/1974 | Zilber |
| 3,920,025 A | 11/1975 | Stasz et al. |
| 4,044,774 A | 8/1977 | Corbin et al. |
| 4,379,462 A | 4/1983 | Borkan et al. |
| 4,459,989 A | 7/1984 | Borkan |
| 4,492,233 A | 1/1985 | Petrofsky et al. |
| 4,512,351 A | 4/1985 | Pohndorf |
| 4,539,993 A | 9/1985 | Stanton |
| 4,558,703 A | 12/1985 | Mark |
| 4,598,713 A | 7/1986 | Hansjurgens et al. |
| 4,633,889 A | 1/1987 | Talalla et al. |
| 4,649,935 A | 3/1987 | Charmillot et al. |
| 4,688,574 A | 8/1987 | Dufresne et al. |
| 4,719,499 A | 1/1988 | Nishizawa et al. |
| 4,750,499 A | 6/1988 | Hoffer |
| 4,754,759 A | 7/1988 | Allocca |

(Continued)

FOREIGN PATENT DOCUMENTS

SU          596247          3/1978

OTHER PUBLICATIONS

Isgar et al. "Symptoms of irritable bowel syndrome in ulcerative colitis in remission" Gut. Mar. 1983; 24(3):190-2.*

(Continued)

*Primary Examiner* — Mark W Bockelman
(74) *Attorney, Agent, or Firm* — Craig Hoersten; Christopher S. L. Crawford; Peter R. Lando (57) ABSTRACT

The present invention involves a method and a system for using electrical stimulation to treat gastrointestinal and/or eating disorders. More particularly, the method comprises surgically implanting an electrical stimulation lead that is in communication with predetermined thoracic vertebral segments to cause spinal nervous tissue stimulation, thus treating a wide variety of gastrointestinal disorders.

6 Claims, 4 Drawing Sheets

U.S. PATENT DOCUMENTS

| | | | |
|---|---|---|---|
| 4,759,368 | A | 7/1988 | Spanton et al. |
| 5,443,486 | A * | 8/1995 | Hrdlicka et al. ............... 607/59 |
| 5,690,691 | A * | 11/1997 | Chen et al. ..................... 607/40 |
| 5,895,416 | A | 4/1999 | Barreras et al. |
| 5,938,690 | A | 8/1999 | Law et al. |
| 6,026,326 | A | 2/2000 | Bardy |
| 6,027,456 | A | 2/2000 | Feler et al. |
| 6,154,678 | A | 11/2000 | Lauro |
| 6,216,045 | B1 | 4/2001 | Black et al. |
| 6,516,227 | B1 | 2/2003 | Meadows et al. |
| 6,609,031 | B1 | 8/2003 | Law et al. |
| 6,620,151 | B2 | 9/2003 | Blischak et al. |
| 6,666,845 | B2 | 12/2003 | Hooper et al. |
| 6,690,397 | B1 | 2/2004 | Daignault, Jr. |
| 6,748,276 | B1 | 6/2004 | Daignault, Jr. et al. |
| 6,754,539 | B1 | 6/2004 | Erickson et al. |
| 6,766,578 | B1 | 7/2004 | Swanson et al. |
| 7,142,923 | B2 | 11/2006 | North et al. |
| 7,200,443 | B2 | 4/2007 | Faul |
| 7,251,529 | B2 | 7/2007 | Greenwood-Van Meerveld |
| 2001/0023368 | A1 | 9/2001 | Black et al. |
| 2003/0083724 | A1 | 5/2003 | Jog et al. |
| 2003/0144708 | A1 | 7/2003 | Starkebaum |
| 2003/0181958 | A1 | 9/2003 | Dobak |
| 2003/0181959 | A1 | 9/2003 | Dobak |
| 2004/0065615 | A1 | 4/2004 | Hooper et al. |
| 2004/0098074 | A1 | 5/2004 | Erickson et al. |
| 2004/0116977 | A1 | 6/2004 | Finch et al. |
| 2004/0147940 | A1 | 7/2004 | Crawford |
| 2004/0153029 | A1 | 8/2004 | Blischak et al. |
| 2004/0230255 | A1 | 11/2004 | Dobak |
| 2006/0036293 | A1 | 2/2006 | Whitehurst et al. |
| 2006/0074456 | A1 | 4/2006 | Pyles et al. |
| 2006/0167498 | A1 | 7/2006 | DiLorenzo |

OTHER PUBLICATIONS

Garcia-Rill et al., "The mesencephalic locomotor region. I. Activation of a medullary projection site," Brain Res., 411:1-12, 1987.

Garcia-Rill, "The basal ganglia and the locomotor regions," Brain Res., 396(1): 47-63, 1986.

Garcia-Rill, et al., "Chemical activation of the mesencephalic locomotor region," Brain Res., 330:43-54, 1985.

Garcia-Rill, et al., "The mesencephalic locomotor region. II. Projections to reticulospinal neurons," Brain Res., 411:13-20, 1987.

Jobling, et al., "Electronic aspects of spinal-cord stimulation in multiple sclerosis," Medical & Biological Engineering & Computing Journal, 18(1): 48-56, 1980.

Kemler, et al., "Relapsing ulcerative colitis associated with spinal cord stimulation," Gastroenterology, 117(1): 215-7, 1999.

Sherwood, "Spinal Cord Stimulation," The encyclopedia of Medical Devices and Instrumentation, J. Webster, Ed., Wiley & Son, New York, vol. 4, pp. 2652-2667, 1988.

Takahashi, Takeo, "Atlas of the Human Body," HarperCollins, p. 132 (1989).

Takahashi, Takeo, "Atlas of the Human Body," HarperCollins, p. 133 (1989).

* cited by examiner

METHOD OF USING SPINAL CORD STIMULATION TO TREAT GASTROINTESTINAL AND/OR EATING DISORDERS OR CONDITIONS

CROSS-REFERENCE TO RELATED APPLICATIONS

This application is a continuation of U.S. application Ser. No. 11/234,960, filed Sep. 26, 2005, pending, which claimed the benefit of U.S. Provisional Application Nos. 60/613,495 filed Sep. 27, 2004 and 60/614,312 filed Sep. 29, 2004, the disclosures of which are fully incorporated herein by reference.

TECHNICAL FIELD

This invention relates to spinal cord stimulation for treating gastrointestinal, disorders, eating disorders, and related conditions, including abdominal pain, gastroparesis, obesity, and pancreatitis.

BACKGROUND OF THE INVENTION

The gastrointestinal ("GI") function is to process and consume food, to extract nutrients and to dispose of waste products of digestion. The digestive system is a twisted shaped tube that starts with the mouth, throat, gullet (esophagus), stomach, ileum (small intestine), colon (large intestine), rectum and anus. This muscular tube is some 25 feet long with most of it coiled within the abdomen. The stomach is a complex organ of the digestive tract (alimentary canal) with the primary functions of dissolution, reduction, and motility of ingested food. Normal contractions of the stomach are the result of three control components: neural activity, chemical activity, and myogenic activity. The neural control component refers to the intrinsic and extrinsic nerves innervating the stomach.

Direct electrical stimulation of the stomach and other portions of the gastric intestinal tract has been experimented with for some time. Most of the experimentation has been oriented toward improving the gastric emptying usually by attempting to speed up or strengthen/reinforce the peristaltic activity through directly placing stimulators on the muscles involved. For example, some of the work has centered on using direct electrical stimulation for the treatment of gastroparesis, or delayed stomach emptying, a condition that is most often a complication of diabetes. Seven million people in the United States may be affected by diabetes, and up to 75% of diabetic patients may experience gastrointestinal dysfunction, including diabetic gastroparesis, a syndrome of delayed gastric emptying, leading to nausea, vomiting, abdominal pain and early satiety.

U.S. Pat. No. 5,423,872 to Cigaina for "Process and Device for Treating Obesity and Syndromes Related to Motor Disorders of the Stomach of a Patient" issued Jun. 3, 1995, describes an implantable gastric electrical stimulator at the antrum area of the stomach which generates sequential electrical pulses to stimulate the entire stomach, thereby artificially altering the natural gastric motility to prevent emptying or slows down food transit through the stomach. U.S. Pat. No. 5,690,691 to Chen et al. for "Gastro-intestinal Pacemaker Having Phased Multi-Point Stimulation" issued Nov. 25, 1997, describes a portable or implantable gastric pacemaker employing a number of electrodes along the greater curvature of the stomach for delivering phased electrical stimulation at different locations to accelerate or attenuate peristaltic movement in the GI tract. U.S. Pat. No. 5,836,994 to Bourgeois for "Method and Apparatus for Electrical Stimulation of the Gastrointestinal Tract" issued Nov. 17, 1998, describes an implantable gastric stimulator which incorporates direct sensing of the intrinsic gastric electrical activity by one or more sensors of predetermined frequency bandwidth for application or cessation of stimulation based on the amount of sensed activity. U.S. Pat. No. 6,091,992 to Bourgeois for "Method and Apparatus for Electrical Stimulation of the Gastrointestinal Tract" issued Jul. 18, 2000 relates to provision of separate electrical pulse trains of differing parameters wherein the pulse trains are composed of a series of at least two pulses. The therapy is applied to promote gastric peristalsis.

U.S. Pat. No. 6,104,955 to Bourgeois for "Method and Apparatus for Electrical Stimulation of the Gastrointestinal Tract" issued Aug. 15, 2000, relates to a gastric stimulator with reversion to a sensing mode to determine the intrinsic slow wave interval to prevent stimulation when the gastric tract is in inter-digestive phases. U.S. Pat. No. 5,861,014 to Familoni for "Method and Apparatus for Sensing a Stimulating Gastrointestinal Tract On-Demand" issued Jan. 19, 1999, relates to an implantable gastric stimulator for sensing abnormal electrical activity of the gastrointestinal tract so as to provide electrical stimulation for a preset time period or for the duration of the abnormal electrical activity to treat gastric rhythm abnormalities.

Despite the attempts to modulate the gastrointestinal system via direct electrical stimulation, there are still several patients in which this type of stimulation system does not provide relief from their gastrointestinal and/or eating disorder. Thus, the present invention provides a novel method of using spinal cord stimulation to treat gastrointestinal and/or eating disorders or conditions.

BRIEF SUMMARY OF THE INVENTION

The present invention relates to stimulation techniques applied to areas of the spinal cord not considered in the prior art to play a role in gastrointestinal and/or eating disorders. In certain embodiments, the invention uses electrical stimulation to treat gastrointestinal and/or eating disorders.

In one embodiment, the invention provides a method of treating a gastrointestinal and/or eating disorder or condition by stimulating spinal nervous tissue at one or more areas associated with a thoracic vertebral segment. In certain embodiments of the invention, it is contemplated that the stimulation is electrical, chemical, or a combination of both.

The gastrointestinal and/or eating disorder or condition may be further defined as obesity, abdominal pain, pelvic pain, anorexia nervosa or bulimia nervosa, pancreatitis, Crohn's disease, or gastroparesis. In a specific embodiment, the gastroparesis is associated with diabetes.

In another embodiment, the invention provides a method of treating a patient with a gastrointestinal and/or eating disorder or condition comprising the steps of: surgically implanting in the patient a system in communication with spinal nervous tissue at one or more areas associated with a thoracic vertebral segment of the spinal cord; and operating the system to stimulate the spinal nervous, thereby treating the gastrointestinal disorder or condition.

In certain embodiments of the invention, it is contemplated that stimulating spinal nervous tissue comprises stimulating spinal nervous tissue associated with at least one of $4^{th}$ thoracic vertebral segment, the $5^{th}$ thoracic vertebral segment, the 6th thoracic vertebral segment, the 7th thoracic vertebral segment, the 8th thoracic vertebral segment, or the 9th thoracic vertebral segment.

In certain embodiments of the invention, the system comprises an electrode. In specific embodiments of the invention, the stimulation is electrical. It is envisioned that in one procedure for placing the electrode portion of the stimulator lead, the stimulation lead is inserted or implanted in the epidural space at a thoracic level of the spinal cord.

In certain embodiments of the invention, the system comprises an infusion pump in communication with spinal nervous tissue. In a specific embodiment, the methods of the present invention comprise surgically implanting a catheter having a proximal end coupled to a pump and a discharge portion for infusing a dosage of a pharmaceutical, wherein after implantation the discharge portion of the catheter is in communication with spinal nervous tissue associated with a thoracic vertebral segment.

It is contemplated that, in certain embodiments of the invention, the system allows the patient to control the frequency of stimulation. For example, it is envisioned that the stimulating is prior to, during, or after the patient consumes food. Thus, in certain embodiments, the electrical spinal cord stimulation delivers electrical pulses on a substantially continuous basis. Still further, the invention may comprise an external handheld device (a "patient programmer") can be used by the patient to wirelessly communicate with the implanted stimulator system to initiate the electrical stimulation at an appropriate time.

One embodiment of the present invention is a method of increasing gastric motility comprising the steps of: surgically implanting a system in communication with spinal nervous tissue associated with one or more thoracic vertebral segments; and operating the system to stimulate the spinal nervous tissue, thereby affecting (i.e., increasing) gastric motility.

Another embodiment of the present invention is a method of increasing glucagon-like peptide 1 activity in a patient comprising the steps of: surgically implanting in the patient a system in communication with spinal nervous tissue associated with one or more thoracic vertebral segments; and operating the system to stimulate the spinal nervous tissue, thereby increasing glucagon-like peptide 1 activity.

It is also contemplated that the present invention provides a method of treating a gastrointestinal disorder and/or condition comprising the steps of: surgically implanting an electrical stimulation lead having a proximal end and a stimulation portion, wherein after implantation the stimulation portion is in communication with spinal nervous tissue associated with one or more thoracic vertebral segments; coupling the proximal end of the lead to a signal generator; and generating an electrical signal with the signal generator wherein said signal electrically stimulates the spinal nervous, thereby treating the gastrointestinal disorder and/or condition.

In certain embodiments of the invention, the stimulating results in modulation of gastric and/or gastrointestinal activity.

It is contemplated that the present invention provides a method and system of treating a wide variety of eating and/or gastrointestinal disorders and/or conditions such as heartburn, bloating, postoperative ileus, abdominal pain and discomfort, early satiety, abdominal pain, epigastric pain, nausea, vomiting, burbulence, regurgitation, intestinal pseudoobstruction, anal incontinence, gastroesophageal reflux disease, irritable bowel syndrome, dyspepsia, chronic constipation, gastroparesis, ulcerative colitis, pancreatitis, Crohn's disease, menstrual cramps, spastic and interstitial cystitis and ulcers, obesity, anorexia nervosa, and bulimia nervosa.

In one embodiment, it is envisioned that the method of the present invention is useful for a patient has previously failed pharmaceutical therapy or direct gastric stimulation therapy for gastroparesis.

The present invention also provides a system for treating a gastrointestinal disorder and/or condition comprising: a probe having a stimulation portion in communication with spinal nervous tissue associated with one or more thoracic vertebral; and a device to stimulate the probe thereby stimulating the spinal nervous, and treating the gastrointestinal disorder and/or condition.

Another embodiment of the invention is a system for treating subjects with gastrointestinal disorders and/or conditions comprising: an electrical stimulation lead that is implanted into the subject's spinal, the lead comprises at least one electrode that is in communication with spinal nervous tissue associated with one or more thoracic vertebral segments; and a signal generator that generates signals for transmission to the electrode of the lead resulting in delivery of electrical signals to the spinal nervous tissue, thereby treating the gastrointestinal disorder and/or conditions.

Yet further, another embodiment of the present invention comprises a method of treating gastoparesis, comprising: implanting at least an electrical lead within a patient such that at least one electrode of the electrical lead is disposed adjacent to nerve tissue associated with a thoracic vertebral segment; selecting a plurality of operating parameters for an electrical spinal cord stimulation system that are effective for treating gastoparesis; programming the electrical spinal cord stimulation system according to the plurality of operating parameters; and activating the electrical spinal cord stimulation system to deliver electrical pulses to the electrode adjacent to nerve tissue associated with the thoracic vertebral segment thereby treating the patient's gastoparesis. More specifically, the at least one electrode is disposed within the T5/T6 epidural space of the patient.

The selecting step may comprise the steps of: temporarily delivering electrical pulses according to the plurality of operating parameters to the electrode adjacent to nerve tissue associated with the thoracic vertebral segment; and monitoring gastric activity that occurs while the temporarily delivering is performed, for example, determining gastric motility by measuring pressure generated by contraction of muscles of the stomach and/or small intestine.

In further embodiments, the lead comprises a plurality of electrodes and the plurality of operating parameters include an electrode configuration. A plurality of operating parameters include a pulse amplitude parameter, a pulse width parameter, and a pulse frequency parameter, for example, the pulse frequency parameter is within the range of 10-350 Hz.

Another embodiment comprises a method of treating an eating disorder, comprising: implanting at least an electrical lead within a patient such that at least one electrode of the electrical lead is disposed adjacent to nerve tissue associated with a thoracic vertebral segment; selecting a plurality of operating parameters for an electrical spinal cord stimulation system that are effective for treating the eating disorder; programming the electrical spinal cord stimulation system according to the plurality of operating parameters; and activating the electrical spinal cord stimulation system to deliver electrical pulses to the electrode adjacent to nerve tissue associated with the thoracic vertebral segment thereby treating the patient's eating disorder, for example, obesity, anorexia nervosa, and bulimia nervosa.

In certain embodiments, the electrical spinal cord stimulation delivers electrical pulses on a temporary basis in response to receiving an initiation signal from an external control device operated by the patient. The patient uses the external control device to deliver electrical pulses beginning immediately before the patient begins eating, and stimulation of nerve tissue associated with the thoracic vertebral segment causes an increase in gastric motility.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

It is readily apparent to one skilled in the art that various embodiments and modifications can be made to the invention disclosed in this application without departing from the scope and spirit of the invention.

I. DEFINITIONS

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "abdominal viscera disorder(s)" as used herein includes those condition which affect the smooth muscles of the lower abdomen outside of the GI tract and include but are not limited to those conditions treated by regulation, stabilization and normalization of enterochromaffin cell secretory, pain and motility mechanisms, afferent fiber activity and GI and lower abdominal smooth muscle cells.

The term "constipation" as used herein means a condition characterized by infrequent or difficult evacuation of feces resulting from conditions such as altered GI motility, altered sensation or evacuation functions and altered reabsorption of water.

The term "dyspepsia" as used herein means a condition characterized by symptoms of abdominal pain, epigastric pain, bloating, early satiety, nausea, heartburn and vomiting as a primary gastrointestinal dysfunction or as a complication, and not exclusive to other disorders such as appendicitis, gallbladder disturbances, or malnutrition.

As used herein, the use of the words "epidural space" or "spinal epidural space" is known to one with skill in the art, and refers to an area in the interval between the dural sheath and the wall of the spinal canal. It is contemplated that stimulation leads may be implanted in the epidural space. As used herein, the term "subdural" refers to the space between the dura matter and arachnoid membrane. In certain embodiments of the invention, a stimulation lead may be implanted in the subdural space.

As used in this disclosure, the term "gastrointestinal" and variations of the term, refer to either the whole alimentary tract, including, for example, the esophagus, stomach, duodenum, small intestine, large intestine and rectum, or to any portion or portions of the alimentary tract, as will be understood by those with skill in the art with reference to this disclosure. The gastrointestinal altered motility, sensitivity and secretion and abdominal viscera disorders which may be treated with the above-identified methods and systems include heartburn, bloating, postoperative ileus, abdominal pain and discomfort, early satiety, epigastric pain, nausea, vomiting, burbulence, regurgitation, intestinal pseudoobstruction, anal incontinence, chronic constipation, diabetic gastroparesis, dyspepsia, gastroesophageal reflux disease, irritable bowel syndrome, ulcerative colitis, Crohn's disease, menstrual cramps, pancreatitis, spastic and interstitial cystitis and ulcers and the visceral pain associated therewith.

The term "gastrointestinal disorder or conditions" as used herein includes gastrointestinal altered motility, sensitivity and secretion disorders in which one or more of the symptoms and conditions affect the gastrointestinal tract from the mouth to the anus. Gastrointestinal disorders include, but are not limited to, heartburn, bloating, postoperative ileus, abdominal pain and discomfort, early satiety, epigastric pain, nausea, vomiting, burbulence, regurgitation, intestinal pseudoobstruction, anal incontinence, gastroesophageal reflux disease, irritable bowel syndrome, ulcerative colitis, Crohn's disease, renal disorders, menstrual cramps, pancreatitis, spastic and interstitial cystitis and ulcers and the visceral pain associated therewith. One with skill in the art is aware that any functional gastrointestinal disorder, including but not limited to those associated with gastric motility, is appropriate for treatment with the method and systems of the present invention.

The term "gastroesophageal reflux disease" and "GERD" as used herein means the incidence of, and the symptoms of, those conditions caused by the reflux of the stomach contents into the esophagus. This includes all forms/manifestations of GERD including, but not limited to, erosive and non-erosive GERD, heartburn and other symptoms associated with GERD.

The term "gastroparesis" as used herein means a paralysis of the stomach brought about by a motor abnormality in the stomach which is often manifested as delayed gastric emptying. This can also be a complication of diseases such as diabetes, progressive systemic sclerosis, anorexia nervosa, or myotonic dystrophy. Although diabetes is the most common known cause, gastroparesis can be the result of physical problems, medications, as well as metabolic, smooth muscle and nervous system disorders. For example, physical problems leading to gastroparesis can include scarring from tumors and ulcers, as well as surgery on the vagus nerve or stomach. Certain medications, including Cardizem and other calcium blockers, which slow contractions in the intestine or weaken the stomach, can contribute to gastroparesis. Hypothyroidism is an example of a metabolic disorder associated with gastroparesis. Smooth muscle disorders such as amyloidosis and scleroderma can cause gastroparesis, as can disorders of the nervous system, such as Parkinson's disease and abdominal migraine.

As used herein, the term "in communication" refers to the stimulation lead being adjacent, in the general vicinity, in close proximity, or directly next to or directly on the predetermined stimulation site, such as a level or area of the spinal cord associated with thoracic vertebral segments. Thus, one of skill in the art understands that the lead is "in communication" with the nervous tissue or spinal cord associated with a thoracic vertebral segment if the stimulation results in a modulation of neuronal activity resulting in the desired response, such as modulation of the gastrointestinal and/or eating disorder.

The term "irritable bowel syndrome" and "IBS" as used herein means a disorder of function involving altered motility, sensitivity and secretion involving the small intestine and large bowel associated with variable degrees of abdominal pain, constipation, bloating or diarrhea without bowel inflammation.

The term "ischemic colitis" refers to inflammation of the large intestine (colon) caused by decreased blood flow to the colon.

The terms "mammal," "mammalian organism," "subject," or "patient" are used interchangeably herein and include, but are not limited to, humans, dogs, cats, horses and cows. The preferred patients are humans.

As used herein the term "modulate" refers to the ability to regulate positively or negatively neuronal activity, including but not limited to, neuronal activity via stimulation of the spinal cord or spinal nervous tissue associated with the thoracic vertebral segments which innervates the organs of the abdominal cavity (e.g., stomach, pancreas, spleen, gall bladder, liver, small intestine, large intestine, kidney, or any other tissue associated with the abdominal cavity), as well as the esophagus. Further, the term modulate can be used to refer to an increase, decrease, masking, altering, overriding or restoring neuronal activity, including but not limited to, neuronal activity associated with the thoracic nerve roots. Modulation of neuronal activity, such as that associated with the thoracic nerve roots, can affect pain and/or gastric activity or gastric motility of a subject, abdominal pain, intestinal motility, esophageal motility, among other effects.

As used herein, the term "neuronal" refers to a neuron which is a morphologic and functional unit of the brain, spinal column, and peripheral nerves.

As used herein, the term "pharmaceutical" refers to a chemical or agent that is used as a drug. Thus, the term pharmaceutical and drug are interchangeable.

As used herein, the term "stimulate" or "stimulation" refers to electrical and/or chemical modulation of selected thoracic nervous tissue, thoracic nerve roots, thoracic segments, thoracic levels, or areas of the spinal cord associated with a thoracic vertebral segment.

The phrase "spinal cord stimulation" as used herein includes stimulation of any spinal nervous tissue, including spinal neurons, accessory neuronal cells, nerves, nerve roots, nerve fibers, or tissues, that are associated with the spinal cord. It is contemplated that spinal cord stimulation may comprise stimulation of one or more areas associated with a thoracic vertebral segment.

As used herein, "spinal nervous tissue" refers to nerves, neurons, neuroglial cells, glial cells, neuronal accessory cells, nerve roots, nerve fibers, nerve rootlets, parts of nerves, nerve bundles, mixed nerves, sensory fibers, motor fibers, dorsal root, ventral root, dorsal root ganglion, spinal ganglion, ventral motor root, general somatic afferent fibers, general visceral afferent fibers, general somatic efferent fibers, general visceral efferent fibers, grey matter, white matter, the dorsal column, the lateral column, and/or the ventral column associated with the spinal cord. Spinal nervous tissue includes "spinal nerve roots," which comprise the 31 pairs of nerves that emerge from the spinal cord. Spinal nerve roots may be cervical nerve roots, thoracic nerve roots, and lumbar nerve roots.

Figure 3A:
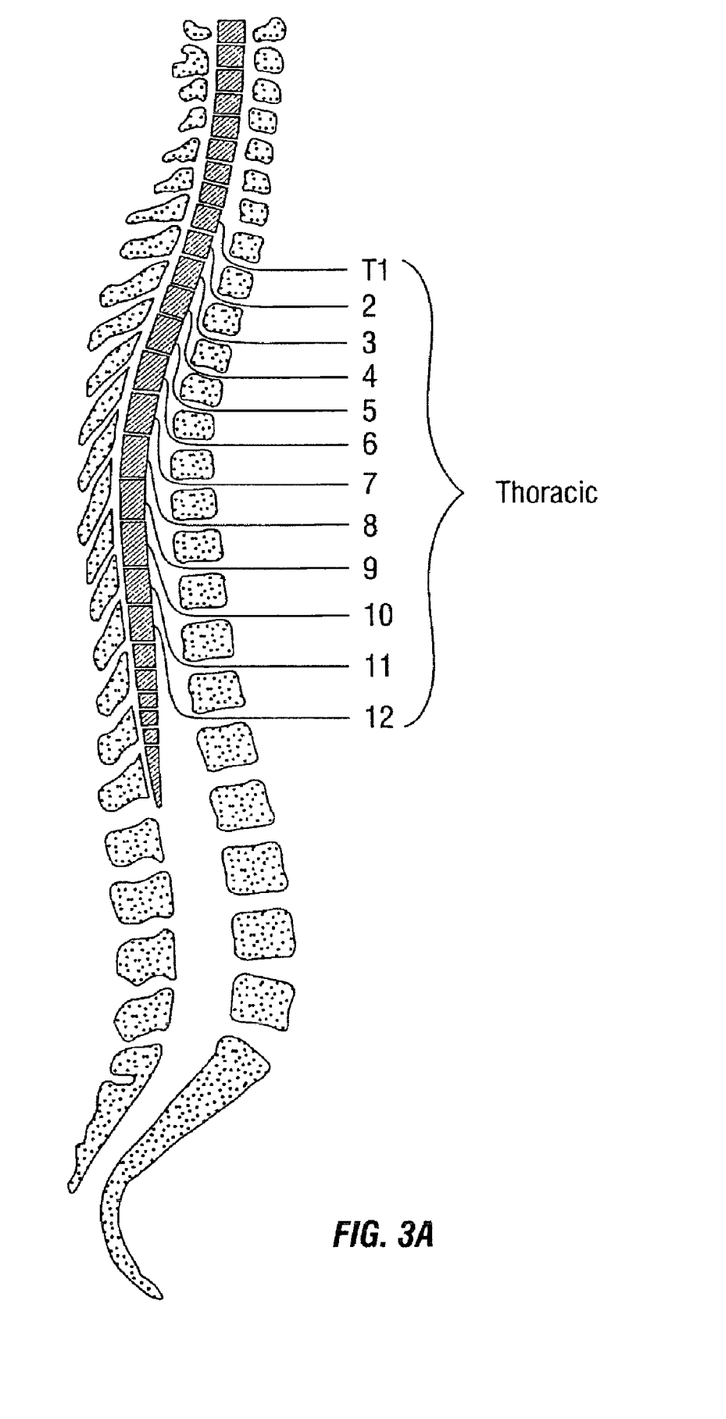
FIGS. 3A and 3B illustrate a spinal cord diagram.
Figure 3B:
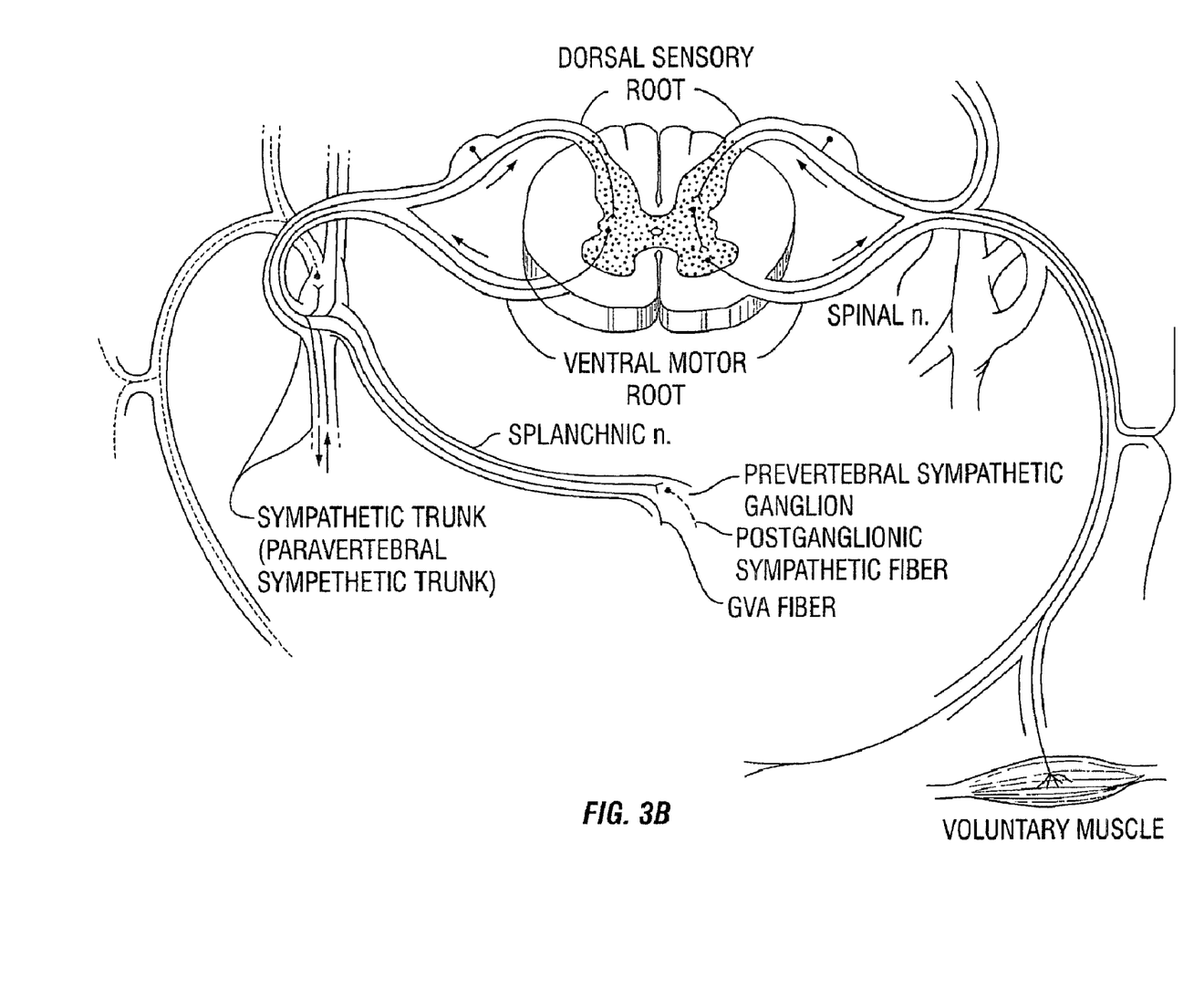

As used herein, "spinal nervous tissue associated with a thoracic vertebral segment," or "nervous tissue associated with a thoracic vertebral segment" or "spinal cord associated with a thoracic segment or level" includes any spinal nervous tissue associated a thoracic vertebral level or segment, which can include at least one thoracic nerve root and tissue associated therewith. Those of skill in the art are aware that the spinal cord and tissue associated therewith are associated with cervical, thoracic and lumbar vertebrae. In the present invention, the spinal cord or spinal tissue that is stimulated is associated with at least one or more of the 12 thoracic vertebra. See also FIGS. 3A and 3B. As used herein, T1 refers to thoracic vertebral segment 1, T2 refers to thoracic vertebral segment 2, T3 refers to thoracic vertebral segment 3, T4 refers to thoracic vertebral segment 4, T5 refers to thoracic vertebral segment 5, T6 refers to thoracic vertebral segment 6, T7 refers to thoracic vertebral segment 7, T8 refers to thoracic vertebral segment 8, T9 refers to thoracic vertebral segment 9, T10 refers to thoracic vertebral segment 10, T11 refers to thoracic vertebral segment 11, and T12 refers to thoracic vertebral segment 12, unless otherwise specifically noted.

As used herein, "thoracic nerve roots," "nerves or nerve roots associated with a thoracic vertebral segment," or "nerve roots associated with a thoracic vertebral level," refer to nerves associated with levels, or segments of the thoracic vertebrae. Thoracic nerve roots are numbered according to the vertebrae below which they emerge. Thus, one with skill in the art realizes that the T5 nerve root emerges between the T5 vertebra and T6 vertebra, and the T6 nerve root emerges between the T6 vertebra and T7 vertebra, and so on. One with skill in the art realizes that due to aberrants (missing ribs) or genetic variations, the exiting of the nerve may be altered in individual subjects, and the above serves as a general guideline.

As used herein, the term "treating" and "treatment" refers to stimulating certain nervous tissue of the spinal cord so that the subject has an improvement in the disease, for example, beneficial or desired clinical results. For purposes of this invention, beneficial or desired clinical results include, but are not limited to, alleviation of symptoms, alleviation of pain, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. ELECTRICAL STIMULATION SYSTEMS

In general terms, stimulation system 10 includes an implantable pulse generator or stimulation source 12 and an implantable electrode, i.e., an electrical stimulation lead, 14 for applying the stimulation signal to the target the spinal cord. In operation, both of these primary components are implanted in the person's body. Stimulation source 12 is coupled to a connecting portion 16 of electrical stimulation lead 14. Stimulation source 12 controls the electrical signals transmitted to electrodes 18 located on a stimulating portion 20 of electrical stimulation lead 14, located adjacent the target thoracic segment, according to suitable signal parameters (e.g., duration, intensity, frequency, etc.). A doctor, the patient, or another user of stimulation source 12 may directly or indirectly input signal parameters for controlling the nature of the electrical stimulation provided. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site to stimulate spinal nervous tissue, according to suitable stimulation parameters (e.g., duration, amplitude or intensity, frequency, pulse width, etc.).

Figure 1A:
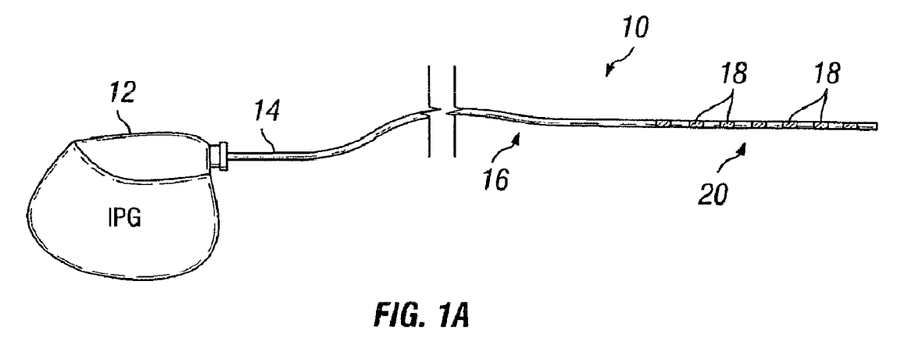
FIGS. 1A and 1B illustrate example electrical stimulation systems.
Figure 1B:
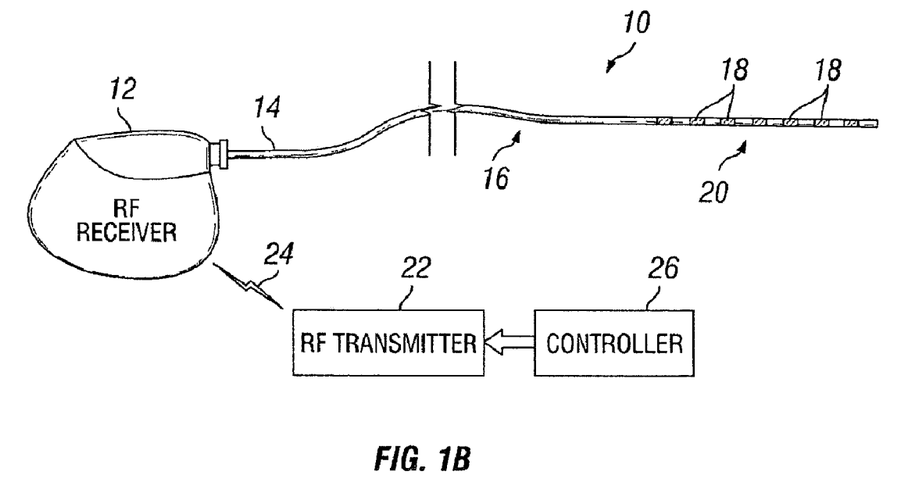
Figure 2A:
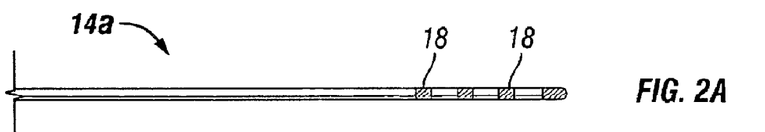
FIGS. 2A-2I illustrate example electrical stimulation leads that may be used in the present invention.
Figure 2B:
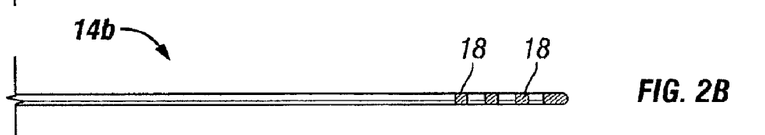
Figure 2C:
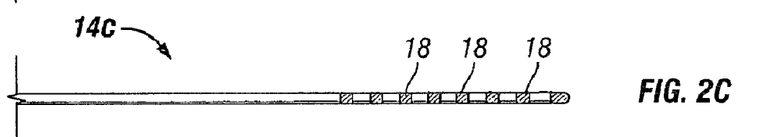
Figure 2D:
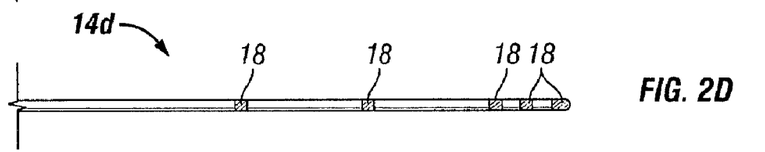
Figure 2E:
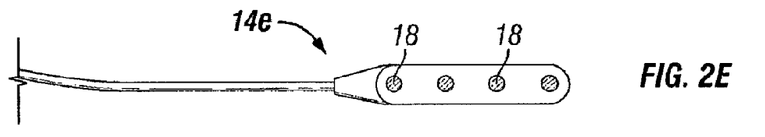
Figure 2F:
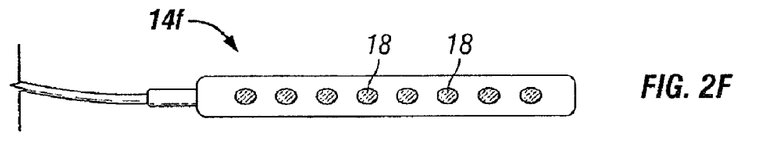
Figure 2G:
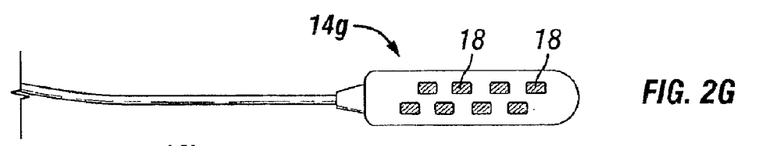
Figure 2H:
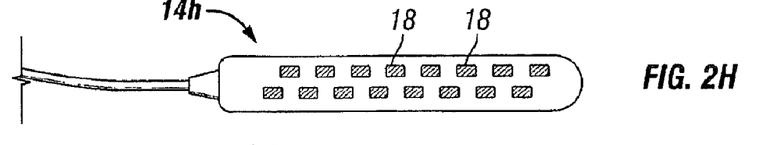
Figure 2I:
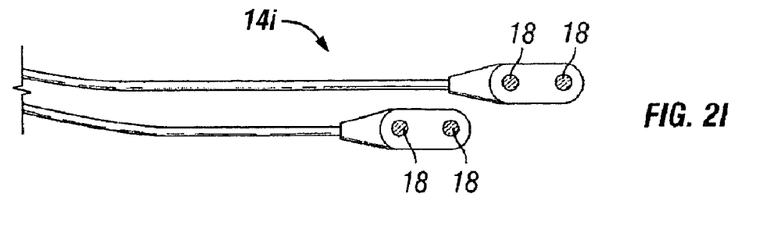

In one embodiment, as shown in FIG. 1A, stimulation source 12 includes an implantable pulse generator (IPG). One of skill in the art is aware that any commercially available implantable pulse generator can be used in the present invention, as well as a modified version of any commercially available pulse generator. Thus, one of skill in the art would be able to modify an IPG to achieve the desired results. An exemplary IPG is one that is manufactured by Advanced Neuromodulation Systems, Inc., such as the Genesis® System, part numbers 3604, 3608, 3609, and 3644. Another example of an IPG is shown in FIG. 1B, which shows stimulation source 12 including an implantable wireless receiver. An example of a wireless receiver may be one manufactured by Advanced Neuromodulation Systems, Inc., such as the Renew® System, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site. Thus, the external controller 26 can be for example, a handheld programmer, to provide a means for programming the IPG. An example wireless transmitter 122 may be one manufactured by Advanced Neuromodulation Systems, Inc., such as the Renew® System, part numbers 3508 and 3516.

FIGS. 2A-2I illustrate example stimulation leads 14 that may be used for electrically stimulating the spinal nervous tissue. As described above, each of the one or more stimulation leads 14 incorporated in stimulation system 10 includes one or more stimulation electrodes 18 adapted to be positioned in communication with the predetermined site of the spinal cord and used to deliver to the stimulation pulses received from stimulation source 12. A percutaneous stimulation lead 14, such as example stimulation leads 14A-D, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions. A laminotomy, paddle, or surgical stimulation lead 14, such as example stimulation leads 14E-I, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, the present invention contemplates stimulation system 10 including any suitable type of stimulation lead 14 in any suitable number. In addition, stimulation leads 14 may be used alone or in combination.

In one embodiment, the stimulation source is transcutaneously in communication with the electrical stimulation lead. In "transcutaneous", electrical nerve stimulation (TENS) the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

Whether using percutaneous leads, laminotomy leads, or some combination of both, the leads are coupled to one or more conventional neurostimulation devices, or signal generators. The devices can be totally implanted systems and/or radio frequency (RF) systems. An example of an RF system is a Renew® system manufactured by Advanced Neuromodulation Systems, Inc.

In one embodiment of the invention, stimulation systems that combine a pulse generator and electrodes for tissue stimulation in a single system may be used. The Bion® stimulator is an example of one such systems that are known in the art. A contemplated stimulation system may have no leads, with the electrodes directly connected to the pulse generator. Alternatively, in another embodiment, a stimulation system with flexible leads is also contemplated. One with skill in the art realizes that the methods of the present invention are appropriate for use with any stimulation device capable of providing stimulation to spinal nervous tissue.

The preferred neurostimulation systems should allow each electrode of each lead to be defined as a positive, a negative, or a neutral polarity. For each electrode combination (i.e., the defined polarity of at least two electrodes having at least one cathode and at least one anode), an electrical signal can have at least a definable amplitude (i.e., voltage), pulse width, and frequency, where these variables may be independently adjusted to finely select the sensory transmitting nerve tissue required to inhibit transmission of neuronal signals. Generally, amplitudes, pulse widths, and frequencies are determinable by the capabilities of the neurostimulation systems. Signal frequencies for this application may be between 10-25,000 Hz, and in one embodiment approximately 50 Hz-3,000 Hz, and in a preferred embodiment between 10-350 Hz.

It is envisaged that the patient will require intermittent assessment with regard to patterns of stimulation. Different electrodes on the lead can be selected by suitable computer programming, such as that described in U.S. Pat. No. 5,938, 690, which is incorporated by reference in its entirety. Utilizing such a program allows an optimal stimulation pattern to be obtained at minimal voltages. This ensures a longer battery life for the implanted systems.

III. IMPLANTATION OF ELECTRICAL STIMULATION SYSTEMS

Pain-managing or disease-managing electrical energy is commonly delivered through electrodes positioned external to the dura layer surrounding the spinal cord. Stimulation on the surface of the cord (subdurally) is also contemplated, for example, stimulation may be applied to the dorsal columns as well as to the dorsal root entry zone. The electrodes are carried by two primary vehicles: a percutaneous leads and a laminotomy lead. Percutaneous leads commonly have two or more, equally-spaced electrodes, which are placed above the dura layer through the use of a Touhy-like needle. For insertion, the Touhy-like needle is passed through the skin, between desired vertebrae, to open above the dura layer. For unilateral pain, percutaneous leads are positioned on a side of a dorsal column corresponding to the "afflicted" side of the body, as discussed above, and for bilateral pain, a single percutaneous lead is positioned along the patient midline (or two or more leads are positioned on each side of the midline). An example of an eight-electrode percutaneous lead is an OCTRODE® lead manufactured by Advanced Neuromodulation Systems, Inc.

Laminotomy leads have a paddle configuration and typically possess a plurality of electrodes (for example, two, four, eight, or sixteen) arranged in one or more columns. An example of a sixteen-electrode laminotomy lead is shown in FIG. 2.

Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place, that tends to migrate less in the operating environment of the human body. Unlike the needle-delivered percutaneous leads, laminotomy leads have a paddle configuration. The paddle typically possess a plurality of electrodes (for example, two, four, eight, or sixteen) arranged in some pattern, for example, columns. An example of an eight-electrode, two column laminotomy lead is a LAMITRODE® 44 lead manufactured by Advanced Neuromodulation Systems, Inc. In the context of conventional spinal cord stimulation, the surgical procedure, or partial laminectomy, requires the resection and removal of certain vertebral tissue to allow both access to the dura and proper positioning of a laminotomy lead. Depending on the position of insertion, however, access to the dura may only require a partial removal of the ligamentum flavum at the insertion site. In a preferred embodiment, two or more laminotomy leads are positioned within the epidural space of T5/T6 or T6/T7 or T7/T8 or T8/T9. The leads may assume any relative position to one another.

One technique that offers the ability to affect neuronal function is the delivery of electrical stimulation for neuromodulation directly to target tissues via an implanted system having a probe. Another technique that offers the ability to affect neuronal function is the delivery of electrical stimulation for neuromodulation directly to target tissues via an implanted system having a stimulation lead. The electrode assembly of the stimulation system may be one electrode, multiple electrodes, or an array of electrodes in or around the target area. The proximal end of the probe or lead is coupled to the system to stimulate the target site. Thus, the probe or lead is coupled to an electrical signal source which, in turn, is operated to stimulate the predetermined treatment site.

IV. INFUSION PUMPS

In further embodiments, it may be desirable to use a drug delivery system independent of or in combination with the electrical stimulation systems described herein. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, without being bound to a specific procedure, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any type of infusion pump can be used in the present invention. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 which are incorporated by reference in its entirety. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

In certain embodiments, the catheter can be in the form of a lead catheter combination, similar to the ones described in U.S. Pat. No. 6,176,242 and U.S. Pat. No. 5,423,877, which are incorporated herein by reference in their entirety.

V. COMBINATION TREATMENT

In order to increase the effectiveness of the electrical stimulation method of the present invention, it may be desirable to combine electrical stimulation with chemical stimulation to treat the gastrointestinal and/or eating disorders.

In one preferred alternative, an implantable signal generator and electrical stimulating lead and an implantable pump and catheter(s) are used to deliver electrical stimulation and/or one or more stimulating drugs to the above mentioned areas as a treatment for gastrointestinal and/or eating disorders.

Herein, stimulating drugs comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxazid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts and anesthetics (e.g., lidocane) may also be used in combination with electrical stimulation.

VI. GASTROINTESTINAL MOTILITY

In certain embodiments of the invention, it is contemplated that stimulation of spinal nervous tissue associated with one or more thoracic vertebral segments modulates gastric motility. In certain embodiments of the invention, esophageal, stomach, small intestinal, and/or large intestinal motility is altered.

Modulation of esophageal motility may involve the gastroesophageal junction, and in particular the lower esophageal sphincter (LES), which is an involuntary ring-like muscle separating the esophagus from the stomach. The LES rests in a closed position to shut off the end of the esophagus, and is relaxed when in the open state. However, the LES does not have the motility to open on its own, rather it opens briefly by normal physiological function of the esophagus during excitation of the inhibitory nerves of the esophagus. This most commonly occurs during peristalsis when the LES opens to allow food to pass from the esophagus to the stomach. Contracting nerves return the LES to its normally closed position.

Modulation of esophageal motility may be useful for the treatment of disorders such as gastroesophageal reflux disease, stricture, achalasia, diffuse esophageal spasm, esophageal cancer and dysphagia. These esophageal disorders affect the motility of the LES and thereby its ability to open and close normally.

Motility disorders of the esophagus, including those associated with systemic disease such as that of the connective tissue, are normally diagnosed using manometry, may be treated by modulation of the function of the esophageal body, including modulation of peristaltic presence, propagation and vigor, or nonperistaltic contractions, as well as that of the upper and lower esophageal Normal contractions of the stomach are the result of three control components: neural activity, chemical activity, and myogenic activity. The neural control component refers to the intrinsic and extrinsic nerves innervating the stomach. The intrinsic nerves release various neurotransmitters and peptides that control contractions and motility. In certain embodiments of the invention, extrinsic nerves may influence the contractions by the release of modulative substances. The chemical control component refers to the various substances (neurotransmitters, neuromodulators and peptides) released from the nerve endings or endocrine-paracrine cells and glands of the stomach, gall-bladder, or pancreas. These biochemical substances may act directly on the smooth muscle cell or on the nerves to modulate or control the occurrence of contractions and motility. The myogenic control component refers to small electrical oscillations of the smooth muscle cells related to polarization and depolarization of the smooth muscle cells. The myogenic activity is referred to as electrical control activity or slow waves. In the present invention, it is contemplated that modulation of gastric motility may be accomplished by modulating any of the above gastric control components. In a preferred embodiment of the invention, one or more of the above processes are modulated by the methods of the present invention.

Small intestinal motility during digestion comprises segmentation contractions and peristalsis. The interdigestive state is seen between meals, when the lumen is largely devoid of contents. During such times, so-called housekeeping contractions propagate from the stomach through the entire small intestine, sweeping it clear of debris. This complex pattern of motility is also known as the migrating motor complex. Motility in the small intestine, as in all parts of the digestive tube, is controlled predominantly by excitatory and inhibitory signals from the enteric nervous system. These local nervous signals are however modulated by inputs from the central nervous system, and a number of gastrointestinal hormones appear to affect intestinal motility to some degree In the large intestine, the motility patterns comprise segmentation contractions antiperistaltic contractions which propagate toward the ileum, and peristaltic contractions, in addition to influx from the small intestine, facilitate movement of ingesta through the colon. Mass movements constitute a type of motility not seen elsewhere in the digestive tube.

Known also as giant migrating contractions, this pattern of motility is like a very intense and prolonged peristaltic contraction which strips an area of large intestine clear of contents.

In periods between meals, the colon is generally quiescent. Following a meal, colonic motility increases significantly, due to signals propagated through the enteric nervous system—the so called gastrocolic and duodenocolic reflexes, which are manifestation of enteric nervous system control. Additionally, distension of the colon is a primary stimulator of contractions. Several times each day, mass movements push feces into the rectum. This is largely a spinal reflex, and results in reflex relaxation of the internal anal sphincter followed by voluntary relaxation of the external anal sphincter and defecation.

For example, it is contemplated that spinal cord stimulation of one or more areas associated with a thoracic segment is associated with an increase in gastric motility or gastric activity. In another embodiment, it is contemplated that spinal cord stimulation of nervous tissue associated with one or more areas associated with a thoracic segment will cause an increase in expression of neurotransmitters, neuromodulators and peptides or hormones associated with increased gastric motility. In another embodiment, it is contemplated that spinal cord stimulation of nervous tissue associated with one or more areas associated with a thoracic segment will cause an increase in expression of neurotransmitters, neuromodulators or peptides associated with a feeling of fullness, for example glucagon-like peptide-1 (GLP-1). In another embodiment of the invention, it is contemplated that spinal cord stimulation of nervous tissue associated with one or more areas associated with a thoracic segment is associated with modulating gastric activity by modulating gastric secretions, such as gastric hormones and enzymes. In one embodiment of the invention, modulation of gastric motility comprises increasing the levels or activity of gastrin.

VII. METHODS TO TREAT GASTROINTESTINAL AND/OR EATING DISORDERS AND CONDITIONS

Methods of spinal cord stimulation to alleviate pain are well known in the art, particularly for use in treating back pain. However, methods of stimulating spinal nervous tissue associated with one or more thoracic segments in order to treat a gastrointestinal and/or eating disorder are not known in the art, and are, in fact, contrary to conventional wisdom in the art. For example, Kemler et al. reported that spinal cord stimulation was associated with a relapse of ulcerative colitis in a patient in remission. Removal of the stimulator caused the patient to go back into remission. Additionally, other researchers have reported no gastric motility benefits to stimulating the areas of the spinal cord associated with thoracic vertebral segments.

The present invention provides a novel method of treating a gastrointestinal and/or eating disorders and conditions by stimulating neuronal tissue associated with a thoracic vertebral segment. For example, a patient with gastroparesis was treated with spinal cord stimulation of spinal cord or neuronal tissue associated with a thoracic vertebral segment. This patient was recipient of a gastric pacemaker in an attempt to alleviate the patient's symptoms. The gastric pacemaker failed to alleviate the patient's gastroparesis. After the gastric pacemaker was removed, a stimulation system as described was placed in according with the present invention and as is known to those skilled in the art. The stimulation system was implanted and delivered electrical stimulation to spinal cord or neuronal tissue associated with a thoracic vertebral segment. The stimulation relieved the pain associated with the patient's condition, which was unexpected because of the source of the pain, and it treated the patient's nausea and other gastroparesis symptoms, which may be surprising to those skilled in the art. The stimulation also increased the patient's gastric motility, which has allowed the patient to have a normal digestion and bowel movements. Based on the success of using such stimulation methods and systems, the various embodiments of the present invention discussed herein have been conceived and reduced to practice.

In another embodiment, a patient with ulcerative colitis is implanted with a stimulation system as described herein. The stimulation system provides stimulation on demand, as needed by the patient. The patient activates the stimulation system when any pain or nausea is experienced. The patient has increased gastric motility and decreased pain or nauseas associated with ulcerative colitis. The patient is able to normalize bowel function.

In another embodiment, a morbidly obese patent is implanted with a stimulation system as described herein. The stimulation system is activated just prior to, during or after the ingestion of food. The patient experiences increased gastric motility, which aids digestion. In this embodiment the patient may have increased levels of GLP-1, which contributes to a feeling of satiety.

In another embodiment, an underweight patient suffering from anorexia nervosa is implanted with a stimulation system as described herein. The stimulation system is activated as necessary in order to stimulate gastric activity. The stimulation relieves constipation and normalizes gastric activity. Certain embodiments of the present invention involve a method of treating a gastrointestinal disorder comprising the steps of: surgically implanting an electrical stimulation lead having a proximal end and a stimulation portion, wherein after implantation the stimulation portion is in communication with a predetermined site; coupling the proximal end of the lead to a signal generator; and generating an electrical signal with the signal generator to modulate the predetermined site thereby treating the gastrointestinal disorder.

In certain embodiments, the predetermined site can include one or more areas of the spinal cord or neuronal tissue associated with a thoracic vertebral segment, which innervates the organs of the abdominal cavity (e.g., stomach, pancreas, gall bladder, spleen, small intestine, large intestine, liver, kidney), as well as the esophagus. Exemplary sites includes, the neuronal tissue associated with at least one or more of the thoracic vertebral segments 5-10 (T5, T6, T7, T8, T9, or T10) or any variation thereof such as between segments superior to T5, T5/T6, T6/T7, T7/T8, T8/T9, T9/T10, or inferior T10.

The gastrointestinal disorders or conditions contemplated by the present invention include gastrointestinal altered motility, sensitivity and secretion disorders in which one or more of the symptoms and conditions affect the gastrointestinal tract from the mouth to the anus. Gastrointestinal disorders include, but are not limited to, heartburn, bloating, postoperative ileus, abdominal pain and discomfort, early satiety, epigastric pain, nausea, vomiting, burbulence, regurgitation, intestinal pseudoobstruction, anal incontinence, gastroesophageal reflux disease, irritable bowel syndrome, ulcerative colitis, Crohn's disease, menstrual cramps, pancreatitis, spastic and interstitial cystitis and ulcers and the visceral pain associated therewith. One with skill in the art is aware that any functional gastrointestinal disorder, including but not limited to those associated with gastric motility, is appropriate for treatment with the method and systems of the present invention.

The present invention is also appropriate for treating a variety of eating disorders and conditions, including obesity, anorexia nervosa, and bulimia nervosa. For example, it is contemplated that the method of the present invention may be used to treat patient for obesity, binge eating, or compulsive overeating. A stimulator as described herein can be implanted in the patient. The stimulator may be turned "on," thus activating the electrical stimulation to the appropriate nervous tissue associated with a thoracic vertebral segment, by the patient when feelings of hunger are present. Alternatively, it is contemplated that the patient may use the stimulation in a continuous manner. Still further, an external handheld device (a "patient programmer") can be used by the patient to wirelessly communicate with the implanted stimulator system to initiate the electrical stimulation at an appropriate time.

In one embodiment, it is contemplated that treating gastrointestinal and/or eating disorders or conditions comprises spinal cord stimulation of nervous tissue associated with one or more areas associated with a thoracic segment, which will cause an increase in expression of neurotransmitters, neuromodulators and peptides or hormones associated with increased gastric motility. In another embodiment, it is contemplated that treating gastrointestinal and/or eating disorders or conditions comprises causing an increase in expression of neurotransmitters, neuromodulators or peptides associated with a feeling of fullness, for example glucagon-like peptide-1 (GLP-1) through modulation of spinal nervous tissue.

For patients suffering from anorexia nervosa or bulimia nervosa, complications of these eating disorders include gastrointestinal problems such as substantial delays in gastric emptying as well as constipation. These problems may give rise to significant medical complications and may contribute to increased difficulties with refeeding and weight restoration. It is contemplated that spinal cord stimulation may be used as part of ongoing therapy for anorexia nervosa or bulimia nervosa in order to normalize gastric function.

Further, biliary tract disorders, of the gall bladder or bile ducts, are also contemplated as being treatable by the method of the present invention. For example, cholecystitis, biliary dyskinesia, and cholangitis may be treated by stimulation of the thoracic nerves. Yet further, hepatic disorders, such as cirrhosis, are contemplated as being treatable by the method of the present invention.

The therapeutic system or of the present invention is surgically implanted in the predetermined sites as described in the above sections. One of skill in the art is cognizant that a variety of electrodes or electrical stimulation leads may be utilized in the present invention. It is desirable to use an electrode or lead that contacts or conforms to the target site for optimal delivery of electrical stimulation. One such example, is a single multi contact electrode with eight contacts separated by 2½ mm each contract would have a span of approximately 2 mm. Another example is an electrode with two 1 cm contacts with a 2 mm intervening gap. Yet further, another example of an electrode that can be used in the present invention is a 2 or 3 branched electrode to cover the predetermined site or target site. Each one of these three pronged electrodes have four contacts 1-2 mm contacts with a center to center separation of 2 of 2.5 mm and a span of 1.5 mm According to one embodiment of the present invention, the target site is stimulated using stimulation parameters such as, pulse width of about 1 to about 500 microseconds, more preferable, about 1 to about 90 microseconds; frequency of about 1 to about 50 to about 3,000 Hz, more preferably, about 10 to about 350 Hz; and voltage of about 0.5 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

Applying electrical stimulation to the gastrointestinal tract can have the effect of suppressing appetite but may also produce "intestinal hurry" where the food is passed through the gastrointestinal tract more quickly than normal so as to reduce the body's absorption of nutrients. Gastrointestinal tract hurry can be produced by stimulation of the stomach and/or small intestine Gastrointestinal tract stimulation according to the invention may be continuous, intermittent, or responsive to patient initiation or gastrointestinal tract activity detection.

Yet another object of the present invention is to stimulate the stomach and/or small intestine to produce gastrointestinal hurry where the speed of the passage of food through the gastrointestinal tract is increased so as to reduce the absorption of nutrients as a means to achieve weight loss for obese patients.

Patient outcomes for patients treated by the methods and systems of the present invention may be tested by standard stomach emptying tests, such as radioactive meal digestion, for example as described in U.S. Pat. No. 6,548,043. Gastric motility may be tested by an antro-duodenal motility study, in which a thin tube (one-eighth inch in diameter) is passed through the nose, down the esophagus, through the stomach and into the duodenum, the first part of the small intestine. Sensors in the tube measure the amount of pressure generated when the muscles of the stomach and intestine contract and squeeze tightly around the tube. The greater the contraction of the muscles, the greater the pressure sensed by the tube. All contractions are recorded by a computer for analysis. Contractions are recorded at rest for up to several hours and for one or two hours after a meal. Other contemplated test to study patient outcomes include upper gastrointestinal x-rays, gastric emptying breath tests, and electrogastrograms Patient outcomes may also be tested by health-related quality of life (HRQL) measures: Patient outcome measures that extend beyond traditional measures of mortality and morbidity, to include such dimensions as physiology, function, social activity, cognition, emotion, sleep and rest, energy and vitality, health perception, and general life satisfaction. (Some of these are also known as health status, functional status, or quality of life measures.)

For purposes of this invention, beneficial or desired clinical results include, but are not limited to, alleviation of symptoms, alleviation of pain, diminishment of extent of disease, stabilized (i.e., not worsening) state of disease, delay or slowing of disease progression, amelioration or palliation of the disease state, and remission (whether partial or total), whether objective or subjective.

While the invention has been described herein relative to a number of particularized embodiments, it is understood that modifications of, and alternatives to, these embodiments, such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 10 into a person for electrical stimulation of the spinal cord.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Treatment of Gastroparesis

Five patient with gastroparesis were implanted with a spinal cord stimulator in the T5/T6 epidural space. After continuous stimulation for 24-48 hours, the patients reported normal gastric emptying and bowel function.

Example 2

Treatment of Abdominal Pain

Patient with gastroparesis was implanted with a spinal cord stimulator in the T5/T6 epidural space. After continuous stimulation for 48 hours, the patient reported a complete absence of abdominal pain and gastroparesis-related nausea.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 3,654,933
U.S. Pat. No. 4,539,993
U.S. Pat. No. 3,724,467
U.S. Pat. No. 4,558,703
U.S. Pat. No. 3,822,708
U.S. Pat. No. 4,598,713
U.S. Pat. No. 3,920,025
U.S. Pat. No. 4,649,935
U.S. Pat. No. 4,044,774
U.S. Pat. No. 4,379,462
U.S. Pat. No. 4,688,574
U.S. Pat. No. 4,459,989
U.S. Pat. No. 4,719,499
U.S. Pat. No. 4,492,233
U.S. Pat. No. 4,750,499
U.S. Pat. No. 4,512,351.
U.S. Pat. No. 4,754,759
U.S. Pat. No. 4,759,368
U.S. Pat. No. 5,938,690
U.S. Pat. No. 6,027,456
U.S. Pat. No. 6,154,678
U.S. Pat. No. 6,216,045
U.S. Pat. No. 6,609,031
U.S. Pat. No. 6,620,151
U.S. Pat. No. 6,666,845
U.S. Pat. No. 6,690,397
U.S. Pat. No. 6,748,276
U.S. Pat. No. 6,754,539
U.S. Pat. No. 6,766,578
U.S. Patent Publication No. 20040153029
U.S. Patent Publication No. 20040147940
U.S. Patent Publication No. 20040116977
U.S. Patent Publication No. 20040098074
U.S. Patent Publication No. 20040065615
U.S. Patent Publication No. 20030083724
U.S. Patent Publication No. 20010023368
Russian Patent No. 596,247
Kemler et al., Gastroenterology. 1999 July; 117(1):215-7
Jobling et al., Medical & Biological Engineering & Computing Journal, January 1980, pp. 48-56.
Garcia-Rill, E., Brain Res. Rev., 11:47-63, 1986;
Garcia-Rill, E. and R. D. Skinner, Brain Res., 411:1-12, 1987a;
Garcia-Rill, E. and R. D. Skinner, Brain Res., 411:13-20, 1987b;
Garcia-Rill, E., R. D. Skinner and J. A. Fitzgerald, Brain Res., 330:43-54, 1985;
Sherwood, A. M., "Spinal Cord Stimulation", The Encyclopedia of Medical Devices and Instrumentation, J. Webster, Ed., Wiley & Son, New York, Vol. 4, pp. 2652-2667, 1988.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

We claim:

1. A method of treating irritable bowel syndrome using an electrical spinal cord stimulation system, comprising:
    implanting an electrical lead within the thoracic T5, T5/T6 or T6 epidural space of the spinal cord of a patient;
    selecting a plurality of operating parameters for the electrical spinal cord stimulation system that are effective for treating irritable bowel syndrome;
    programming the electrical spinal cord system according to the plurality of operating parameters; and
    treating the patient's irritable bowel syndrome by increasing gastric motility by activating the electrical spinal cord stimulation system to deliver electrical pulses to spinal nervous tissue within the thoracic T5, T5/T6 or T6 epidural space of the spinal cord of the patient wherein gastric function is normalized.

2. The method of claim 1 wherein the electrical spinal cord stimulation system delivers electrical pulses on a substantially continuous basis.

3. The method of claim 1 wherein the plurality of operating parameters include a pulse amplitude parameter, a pulse width parameter, and a pulse frequency parameter.

4. The method of claim 3 wherein the pulse frequency parameter is within the range of 10-350 Hz.

5. The method of claim 1 wherein the lead comprises a plurality of electrodes and the plurality of operating parameters include an electrode configuration.

6. The method of claim 1 wherein the patient has decreased nausea.

\* \* \* \* \*